United States Patent
Taron et al.

(10) Patent No.: US 9,895,127 B2
(45) Date of Patent: Feb. 20, 2018

(54) SYSTEMS AND METHODS OF IMAGE ACQUISITION FOR SURGICAL INSTRUMENT RECONSTRUCTION

(71) Applicant: General Electric Company, Schenectady, NY (US)

(72) Inventors: Maxime Taron, Buc (FR); Yves Lucien Trousset, Palaiseau (FR)

(73) Assignee: General Electric Company, Schenectady, NY (US)

(*) Notice: Subject to any disclaimer, the term of this patent is extended or adjusted under 35 U.S.C. 154(b) by 157 days.

(21) Appl. No.: 14/840,906

(22) Filed: Aug. 31, 2015

(65) Prior Publication Data
US 2017/0055928 A1 Mar. 2, 2017

(51) Int. Cl.
*G06T 7/00* (2017.01)
*A61B 6/00* (2006.01)
(Continued)

(52) U.S. Cl.
CPC .............. *A61B 6/5235* (2013.01); *A61B 6/03* (2013.01); *A61B 6/12* (2013.01); *A61B 6/4014* (2013.01); *A61B 6/4441* (2013.01); *A61B 6/463* (2013.01); *A61B 6/466* (2013.01); *A61B 6/467* (2013.01); *A61B 6/488* (2013.01); *G06T 7/55* (2017.01); *G06T 11/005* (2013.01); *A61B 6/465* (2013.01); *A61B 6/487* (2013.01); *A61B 6/505* (2013.01); *A61B 6/5247* (2013.01);
(Continued)

(58) Field of Classification Search
None
See application file for complete search history.

(56) References Cited

U.S. PATENT DOCUMENTS

2006/0269114 A1* 11/2006 Metz ..................... G06T 11/005
382/131
2007/0021668 A1 1/2007 Boese et al.
(Continued)

FOREIGN PATENT DOCUMENTS

WO 2015121301 A1 8/2015
WO WO 2015121301 A1 * 8/2015 ............... A61B 6/12

OTHER PUBLICATIONS

Automated Determination of Optimal Angiographic Viewing Angles for Coronary Artery Bifurcations from CTA Data. Kitslaar et al. 2008.*

(Continued)

*Primary Examiner* — Delomia L Gilliard
(74) *Attorney, Agent, or Firm* — Andrus Intellectual Property Law, LLP

(57) ABSTRACT

Systems and methods of object reconstruction from x-ray imaging include receiving an input of a first angulation for a first x-ray image. A first score representative of a quality of a reconstruction of an object from an x-ray image acquired at the first angulation is calculated. The first x-ray image is acquired at the first angulation. An input of a second angulation for a second x-ray image is received. A second score representative of the quality of the reconstruction of the object from the first x-ray image and an x-ray image acquired at the second angulation is calculated. The second x-ray image is acquired at the second angulation. The object is reconstructed from the first x-ray image and the second x-ray image.

20 Claims, 10 Drawing Sheets

(51) Int. Cl.
*A61B 6/03* (2006.01)
*A61B 6/12* (2006.01)
*G06T 11/00* (2006.01)
*G06T 7/55* (2017.01)
*A61B 90/00* (2016.01)

(52) U.S. Cl.
CPC .............. *A61B 2090/376* (2016.02); *G06T 2207/10121* (2013.01); *G06T 2210/41* (2013.01)

(56) References Cited

U.S. PATENT DOCUMENTS

| | | |
|---|---|---|
| 2008/0171936 A1 | 7/2008 | Homan et al. |
| 2010/0014740 A1* | 1/2010 | Movassaghi ......... A61B 6/4441 382/132 |
| 2012/0140875 A1* | 6/2012 | Dennerlein ............ A61B 6/032 378/19 |
| 2012/0250964 A1 | 10/2012 | Pfister |
| 2012/0289825 A1* | 11/2012 | Rai ........................ A61B 6/463 600/425 |
| 2016/0275684 A1* | 9/2016 | Elenbaas ............... G06T 7/0028 |

OTHER PUBLICATIONS

European Search Report and Opinion issued in connection with corresponding European Application No. 16185437.7 dated Feb. 8, 2017.

Borst et al., "Accuracy of X-Ray Image-Based 3D Localization from Two C-Arm Views: A Comparison Between an Ideal System and a Real Device", Feb. 6, 2009.

Holm et al., "In vivo assessment of bifurcation optimal viewing angles and bifurcation angles by three-dimensional (3D) quantitative coronary angiography", The International Journal of Cardiovascular Imaging, Dec. 2011.

Kitslaar et al., "Automated determination of optimal angiographic viewing angles for coronary artery bifurcations from CTA data—art. No. 69181J", Proceedings of Spie—The International Society for Optical Engineering, Mar. 2008.

Papalazarou et al., "Surgical Needle Reconstruction Using Small-Angle Multi-View X-Ray", International Conference on Image Processing, Sep. 2010.

* cited by examiner

SYSTEMS AND METHODS OF IMAGE ACQUISITION FOR SURGICAL INSTRUMENT RECONSTRUCTION

BACKGROUND

The present disclosure is related to the field of image processing for 3D display of a patient's organ, and more particularly, to the field of image processing for a 3D display of a patient's organ in which a surgical instrument is positioned.

Techniques exist which enable real-time visualization of a surgical instrument, in situ during a surgical procedure, such as needle, catheter, or a straight or shaped guide wire.

Fluoroscopy image gives real-time knowledge of the position of the surgical instrument. Fluoroscopy imaging uses x-rays to acquire and display two dimensional (2D) images of a region of interest in which a surgical instrument has been inserted.

Fluoroscopy imaging only enables the display of 2D images thereby compelling the practitioner to interpret and mentally reconstruct a 3D image in order to determine the exact position of the surgical instrument within the 3D volume.

Tomographic imaging enables the reconstruction of images in three-dimension (3D) and provides images corresponding to cross-sectional slices of part of the patient's body. Thus, the position of the instrument relative to the patient's body can be directly evaluated.

Although tomographic imaging has advantages, it also has disadvantages. In order to be able to reconstruct a 3D image of the patient's body, several 2D images at different angle positions of a C-arm carrying a radiation source must be acquired. The patient is therefore, subjected to radiation doses. In an effort to limit radiation doses, the 2D images used in the reconstruction of the present disclosure are only acquired at the discretion of the practitioner. This requires registration of the previously reconstructed 3D volume to the current fluoroscopic view. Subsequent movement of the patient may degrade this registration. To further limit the radiation dose, the practitioner may conduct treatment plan instrument trajectory planning as well as instrument position assessment with a reconstructed instrument overlaid on x-ray volume oblique slices. Techniques for instrument reconstruction are available, yet the quality of such instrument reconstruction is inherently limited for at, least the reasons highlighted above regarding reconstruction, as well as ultimately the quality of the x-ray images used to perform such reconstructions.

SUMMARY

An exemplary embodiment of a method of object reconstruction from x-ray images includes receiving an input of a first angulation for a first x-ray. A first score representative of a quality of a reconstruction of an object from an x-ray image acquired at the first angulation is calculated. The first x-ray image is acquired at the first angulation. An input of a second angulation for a second x-ray is received. A second score representative of the quality of the reconstruction of the object from the first x-ray image and an x-ray acquired at the second angulation is calculated. The second x-ray image is acquired at the second angulation. The object is reconstructed from the first x-ray image and the second x-ray image.

A further exemplary embodiment of a method of reconstruction of a surgical instrument includes calculating a first plurality of scores for each of a plurality of possible angulations of a first x-ray from a surgical instrument target trajectory. An input of a first angulation for the first x-ray is received. A first x-ray image at the first angulation is acquired with an x-ray C-arm. A second plurality of scores for each of a plurality of possible angulations of a second x-ray are calculated from the surgical instrument target trajectory and the first x-ray image. An input of a second angulation for the second x-ray is received. A second x-ray image at the second angulation is acquired with the x-ray C-arm. The surgical instrument is reconstructed from the first x-ray image and the second x-ray image.

An exemplary embodiment of a system for surgical instrument reconstruction includes an x-ray C-arm. The x-ray C-arm includes an emitter and a detector. The x-ray C-arm is movable about a plurality of axes and operable to acquire x-ray images of a patient at a plurality of angulations about the plurality of axes. A graphical display is configured to present at least a volume representing patient anatomy. A controller is communicatively connected to the x-ray C-arm and the graphical display. The controller receives an input of a first angulation for a first x-ray, calculates a first score representative of a quality of a reconstruction of the surgical instrument from an x-ray image acquired at the first angulation, and operates the graphical display to present the first score. The controller operates the x-ray C-arm to acquire a first x-ray image. The controller receives an input of a second angulation for a second x-ray, calculates a second score representative of a quality of a reconstruction of the surgical instrument from an x-ray image acquired at the second angulation and the first x-ray image, and operates the graphical display to present the second score. The controller operates the x-ray C-arm to acquire a second x-ray image. The controller reconstructs a surgical instrument from the first x-ray image and the second x-ray image and presents the reconstructed surgical instrument in at least one of a 2D image and a 3D image on the graphical display.

DETAILED DESCRIPTION

Embodiments as disclosed herein are understood to be given as examples and a person of ordinary skill in the art can carry out concepts as disclosed herein in other manners and combinations apart from the specific exemplary embodiments disclosed. Some embodiments may be carried out without all specific features described, therein while individual characteristics of two or more embodiments may be combined to result, in further embodiments within the scope of the present disclosure.

Figure 1:
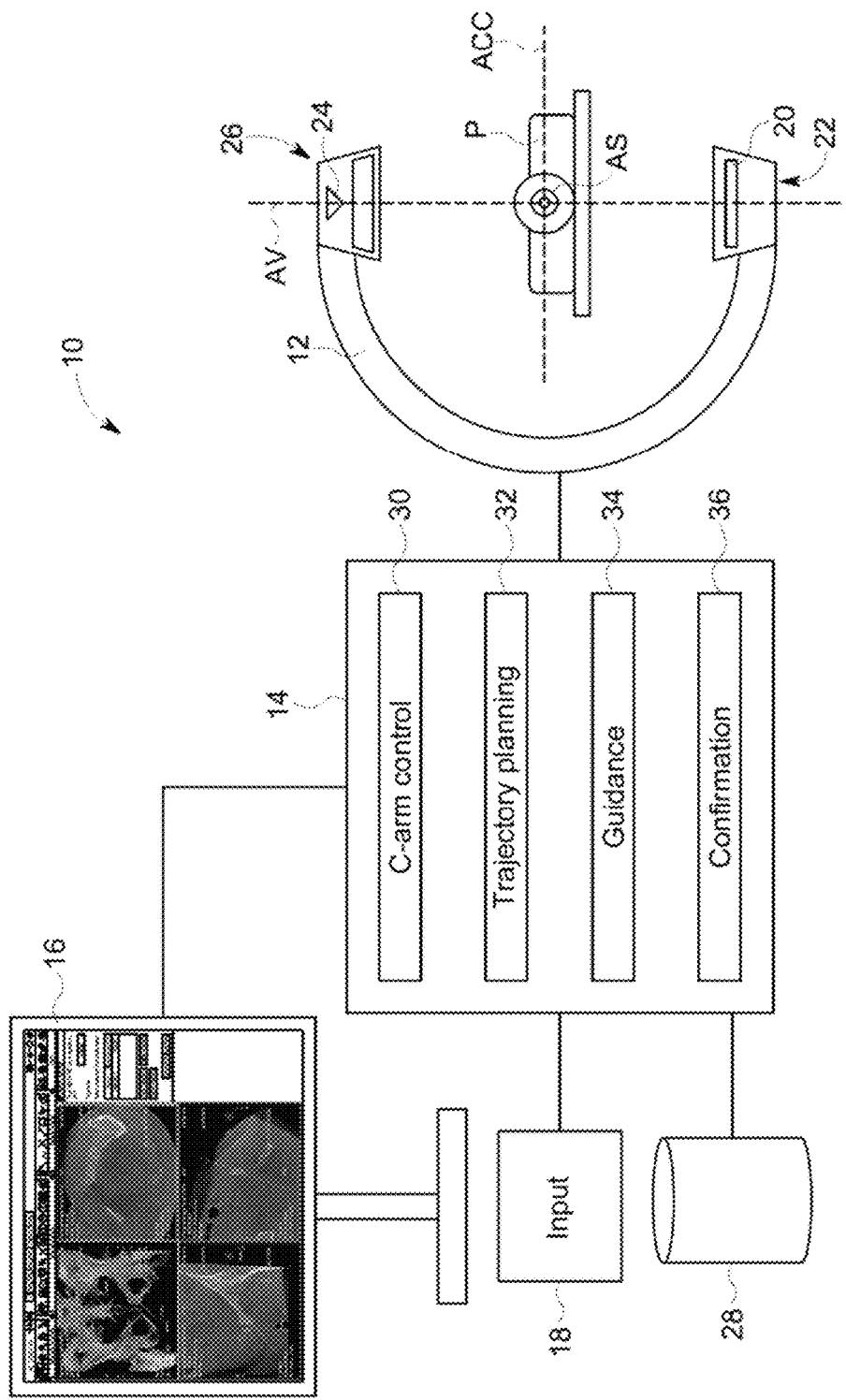
FIG. 1 depicts an exemplary embodiment of an imaging system.

An exemplary embodiment of a medical image system 10 is depicted in FIG. 1. The medical imaging system 10 includes a rotating C-arm 12 which could be positioned in a plurality of angular positions about a patient P. A controller 14 is communicatively connected to the C-arm 12 as well as to a graphical display 16. The controller 14 is further connected to an input device 18, which in embodiments may be a mouse or a keyboard, while in other embodiments it may be a touch-sensitive component of the display 16, or another type of input device as would be recognized by a person of ordinary skill in the art.

The controller 14 operates in the manner as disclosed in further detail herein in order to carry out functionally of the medical imaging system 10, including, but not limited to positioning of the C-arm 12 and any of a plurality of angular positions and capturing, medical images at those positions.

The rotating C-arm 12 is mobile in rotation about axis relative to the patient. The C-arm is exemplarily rotated between a right anterior oblique (RAO) and a left anterior oblique (LAO) angulations about a rotation axis (AS). The C-arm 12 is mobile in rotation between cranial (CRA) and caudal (CAU) angulations about a cranial caudal axis (ACC). The C-arm is further mobile in rotation in a longitudinal (L) movement about a vertical axis (AV) the C-arm 12 is a robot controlled by the controller 14 to position and acquire radiographic images exemplarily with a radiation source 20 positioned at a first end 22 of the C-arm 12 and a detector 24 positioned at a second end 26 of the C-arm 12. The radiation source 20 is capable of emitting radiation (e.g. x-rays) from the first end 22 to the collected at the detector 24 at the second end 26 after passing through the patient P. In modem radiographic systems, the detector 24 is a flat digital sensor that enables the recording of the 2D x-ray images. While a single C-arm 12 is depicted in FIG. 1, it is understood that other medical imaging systems may include more than one C-arm, for example a biplane C-arm.

The medical imaging system 10 further includes a memory 28 which is either integral with or communicatively connected to the controller 14. The memory 28 operates to record parameters and medical images acquired by the medical imaging system 10. If the memory 28 is located outside of the controller 14, the memory 28 and the controller 14 can be connected via a wire connection, a network or port (e.g. a USB port). The memory 28 may be a hard disc or SSD or any other removable, creditable storage device. The memory 28 may be a ROM or RAM app memory of the controller 14, a USB key, a memory card, or a memory located on a centralized server (not depicted).

In embodiments, the controller 14 is embodied by one or more computer processors that execute computer readable code designed to carry out the functions and operations as disclosed herein. These functions and operations as executed by the controller 14 may be grouped into at least four applications or functions as described with respect to the embodiments as disclosed herein. Such applications include C-arm control 30 which includes, but is not limited to both positioning of the C-arm 12 as well as acquisition of images with the C-arm 12 using the emitter 20 and detector 24. Trajectory planning application 32 operates to present a plurality of views of 2D and/or 3D visualizations of patient anatomy to the practitioner for planning a target instrument trajectory. Guidance application 34 acquires fluoroscopy x-ray images exemplarily with the C-arm 12 and presents them with an overlay containing 3D of patient anatomy and optionally with the target trajectory to guide the clinician to the target location within the patient's anatomy. Reconstruction application 36, as described in further detail herein, enables clinicians to assess instrument position relative to the target location. The reconstruction application 36 as described herein operates to reconstruct the instrument within the 3D system and project this reconstructed instrument to 2D and/or 3D images of patient anatomy to confirm instrument position within the patient.

While C-arm controls are used throughout the processes as described herein, in a generalized workflow of the system, the trajectory planning 32, guidance 34, and reconstruction 36 occurs generally sequentially. While exemplary embodiments disclosed herein may be used with a wide variety of guided surgical procedures, those surgical procedures that use an elongated instrument including, but not limited to, a needle, catheter, or straight or a spiral wire guides, as well as others that would be recognized by a person of ordinary skill in the art, images as depicted herein are from an exemplary application of a pelvis bone consolidation. It will be recognized that such systems and methods as disclosed herein may be used in any of a variety of guided surgical procedures using any of the instruments identified above. Work flow of the procedure begins by acquiring an initial 3D volume of a patient. This may exemplarily be performed with cone-beam computed tomography (CBCT) which may be a capability of the C-arm 12. Alternatively, the 3D volume of the patient may come from magnetic resonance (MR) imaging or other 3D imaging techniques.

Figure 2:
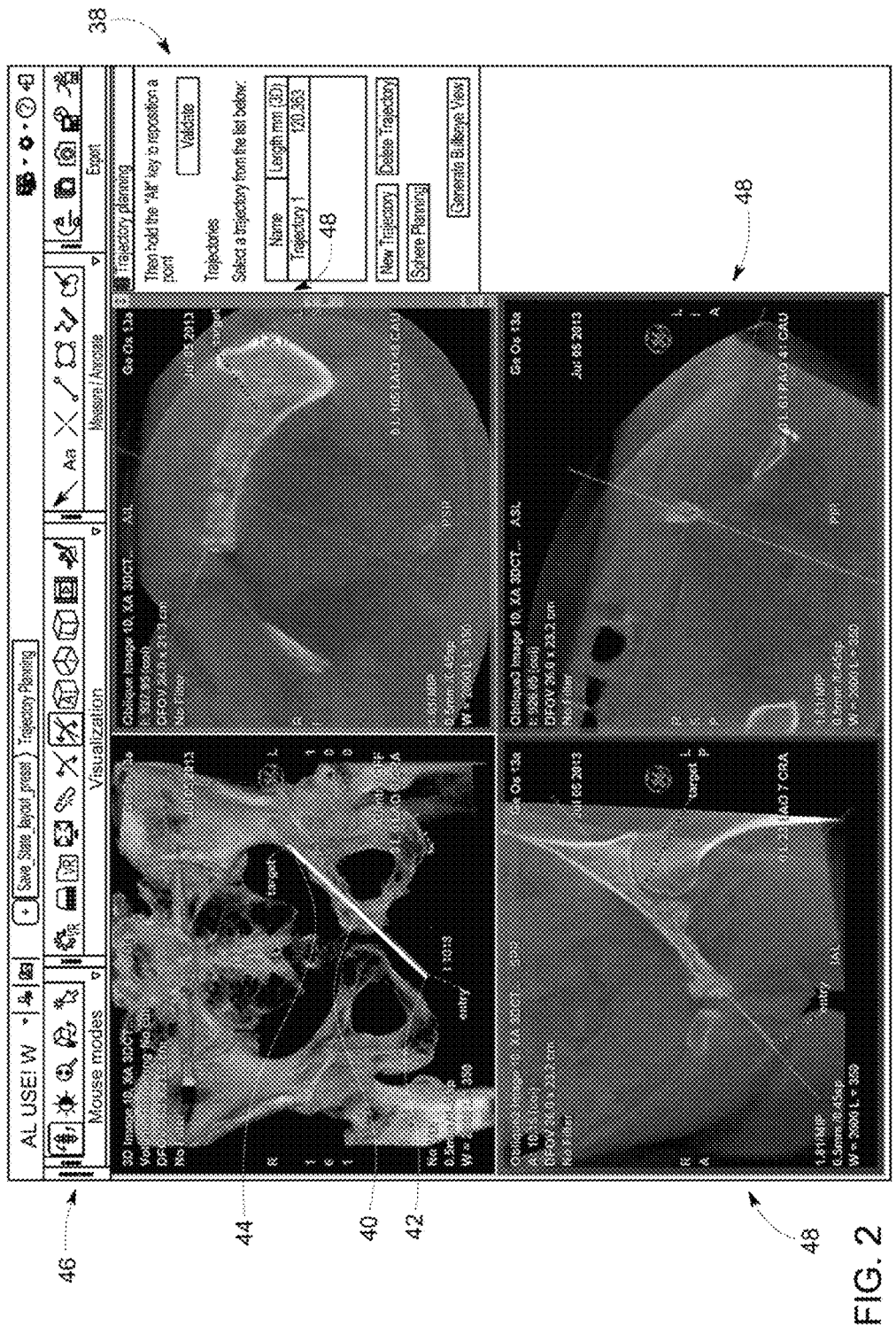
FIG. 2 depicts an exemplary embodiment of a trajectory planning display.

FIG. 2 presents an exemplary embodiment of a trajectory planning display 38. As referenced above, in treatment planning, a target trajectory 40 is determined between an entry point 42 and a target point 44 on the patient's anatomy. The trajectory planning display 38 presents the target trajectory 40 in a variety of views, including the 3D reconstruction 46 and one or more oblique slices 48 of the 3D reconstruction 46.

Figure 3:
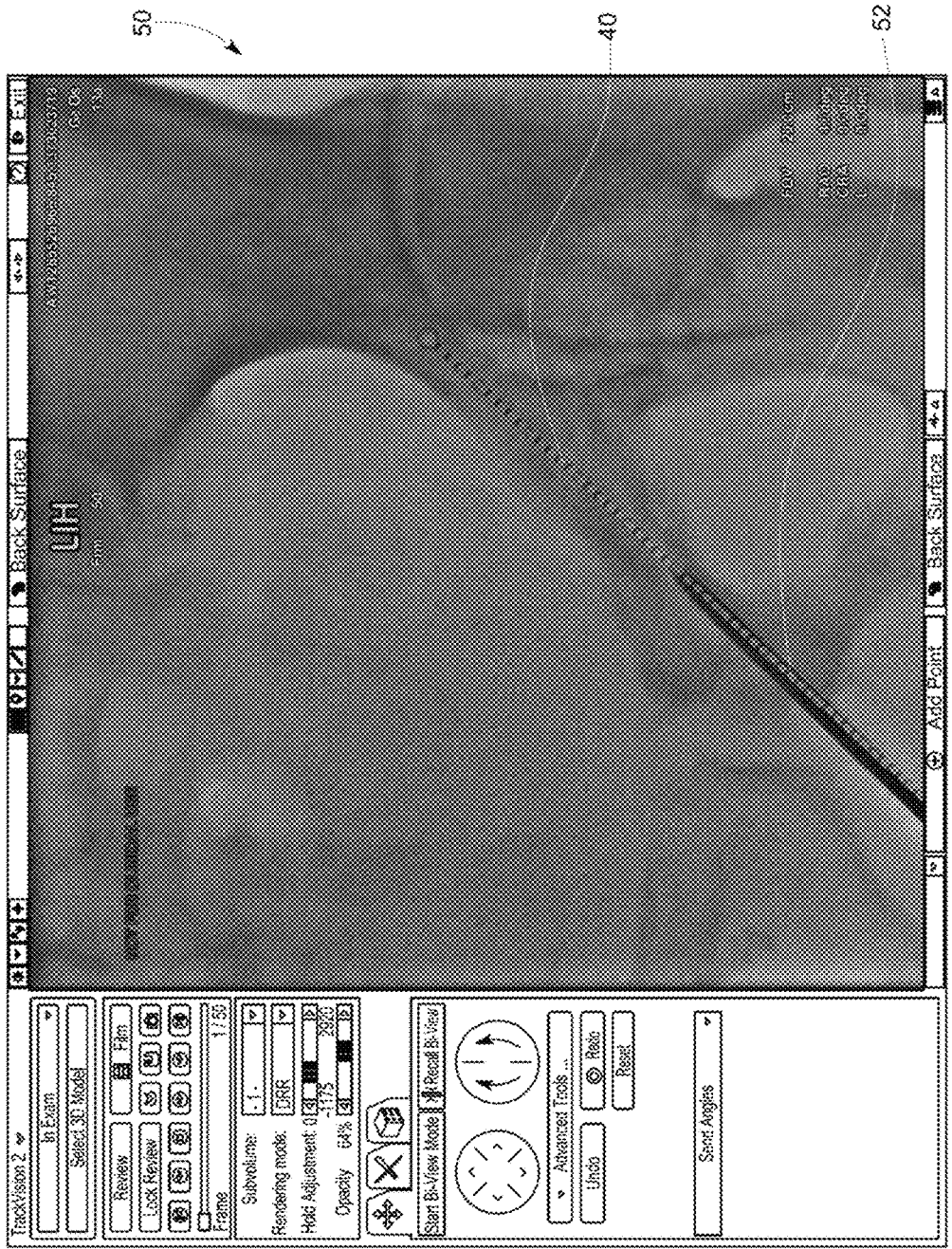
FIG. 3 depicts an exemplary embodiment of a guidance display.

Next, the surgical procedure is initiated and the instrument is entirely or partially inserted into the patient. Fluoroscopy imaging provides guidance and monitoring of the progression of the surgery. In embodiments, a guidance display 50 depicted in FIG. 3 presents the fluoroscopic image with the reconstructed 3D volume registered to the fluoroscopic image. The target trajectory 40 is further superimposed with the 3D reconstruction so that the fluoroscopic image of the needle 52 can be monitored for progression along the target trajectory 40.

During the surgical procedure, the practitioner may desire further 3D confirmation of the instrument position. In such instance, the practitioner will operate a confirmation and reconstruction application as disclosed herein. Exemplarily, a practitioner may desire further positional confirmation upon insertion of an instrument, upon reaching the target point for the instrument, or at any step of the insertion process at which the practitioner desires further confirmation. Vibrations in the fluoroscopic images can impact 3D registration and instrument alignment and instrument guidance. This can be due to patient movement, including shocks to the patient, exemplarily from the force of the instrument, which in the case of a needle in a pelvis bone consolidation is hammered through the pelvis bone. Furthermore, while the instrument guidance is provided with a registered 3D volume, the guidance is still based upon a 2D fluoroscopic view therefore; misalignment relative to the target trajectory 40 in a direction orthogonal to the fluoroscopic view may be unnoticed without 3D confirmation.

Figure 4A:
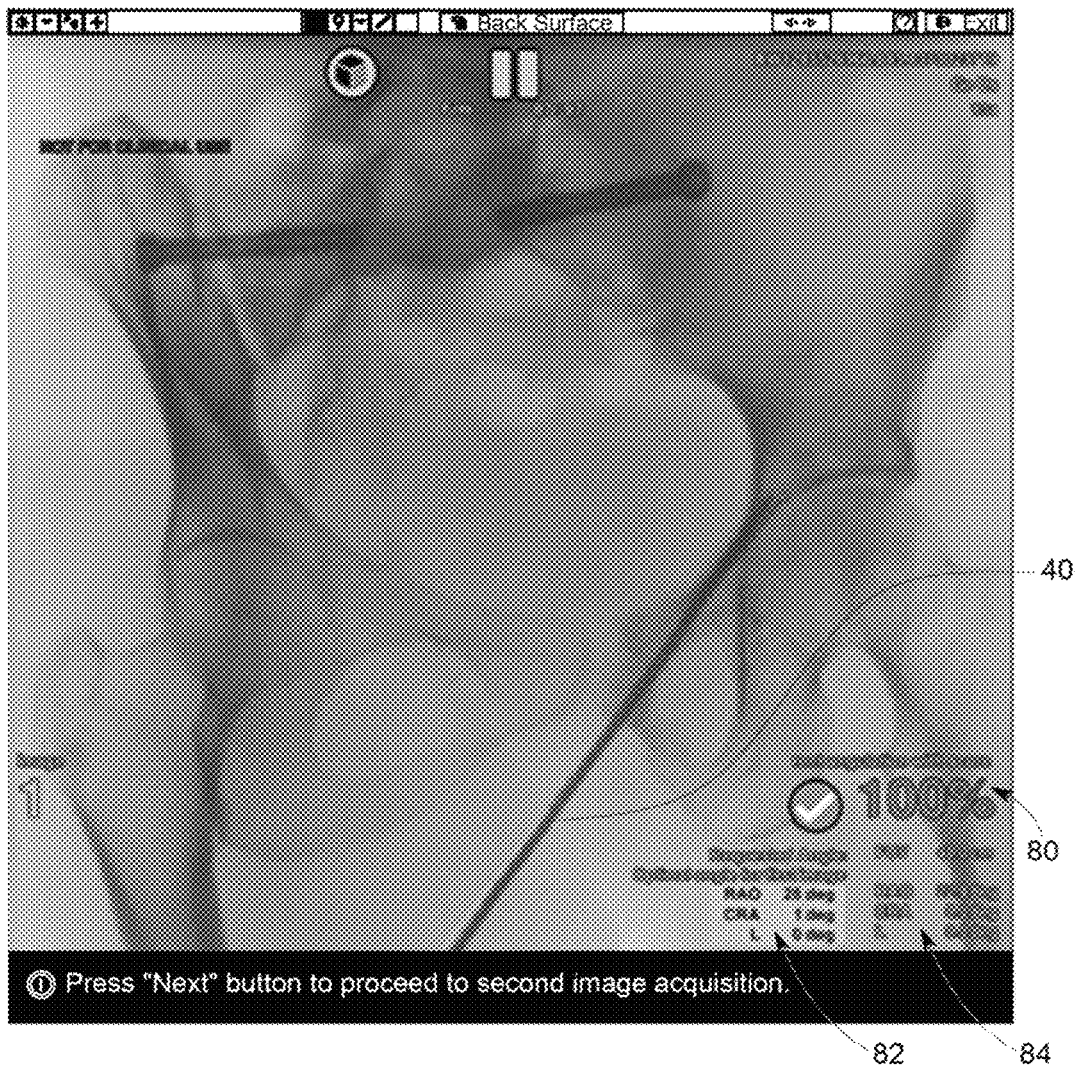
FIG. 4A depicts a display for acquisition of a first image.
Figure 7:
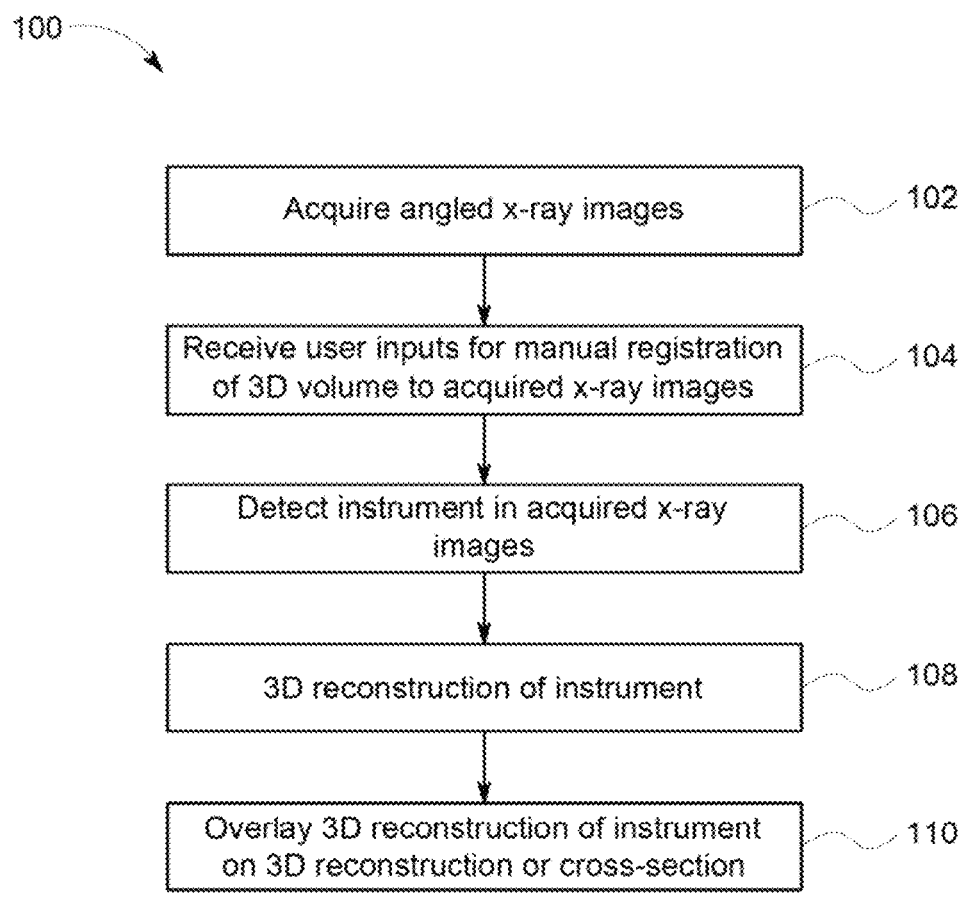
FIG. 7 is a flow chart that depicts an exemplary embodiment a method of performing a 3D reconstruction for instrument confirmation.

FIG. 7 is a flow chart that depicts an exemplary embodiment of a method 100 of performing a 3D reconstruction of an instrument for 3D position confirmation. In the method 100, first angled x-ray images are acquired at 102. FIG. 4A exemplarily depicts a display for acquisition of a first image and FIG. 4B exemplarily depicts a display for acquisition of a second image. In exemplary embodiments, the angled x-ray images can be acquired with the C-arm and will be described in further detail herein. While descriptions found herein primarily focus on embodiments in which two x-ray images are acquired, it is recognized that more than two images may be acquired in other embodiments within the scope of the present disclosure.

After the angled x-ray images are acquired at 102, a 3D volume is registered to the acquired x-ray images at 104. This is exemplarily a manual registration of a relevant portion of the 3D volume acquired during trajectory planning, in an embodiment, the system presents a score of the overall reconstruction accuracy based upon concepts disclosed in further detail herein regarding the accuracy of the angled x-ray images, the registration of the 3D reconstruction, and the target trajectory.

Figure 5:
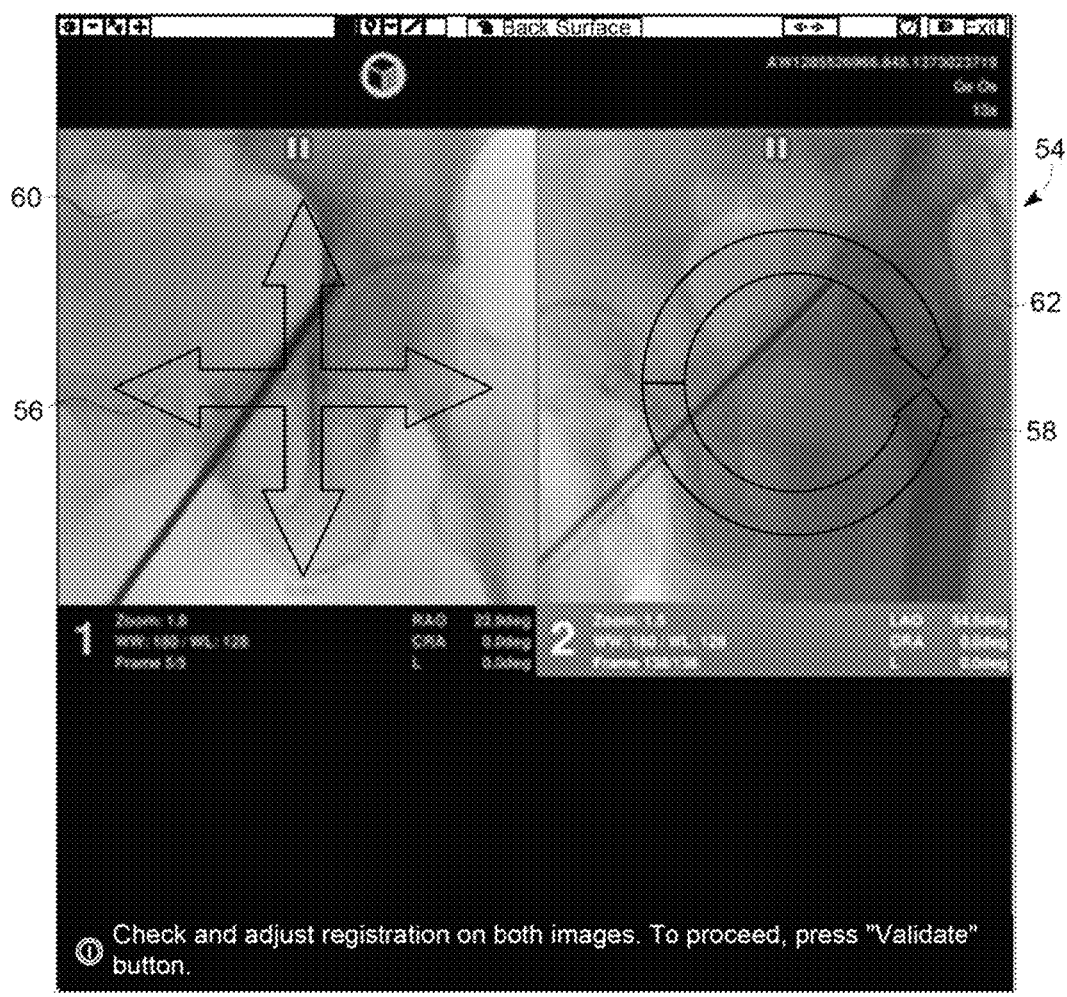
FIG. 5 depicts an exemplary embodiment of a registration display.

As depicted in the registration display 54 of FIG. 5 the manual registration may include user inputs of translation 56 or rotation 58 relative to the respective first image 60 and second image 62 to align the 3D volume on the x-ray images. In embodiments, such manual registration has been found to consistently produce accuracy within one millimeter of alignment between the 3D volume and the x-ray image.

Next, at 106 the instrument, is detected in the acquired x-ray images. This may be automated performed using image processing techniques to automatically detect the object representing an instrument closest to the target trajectory. At 108 a 3D reconstruction of the detected instrument is performed by intersection back projection planes.

Figure 6:
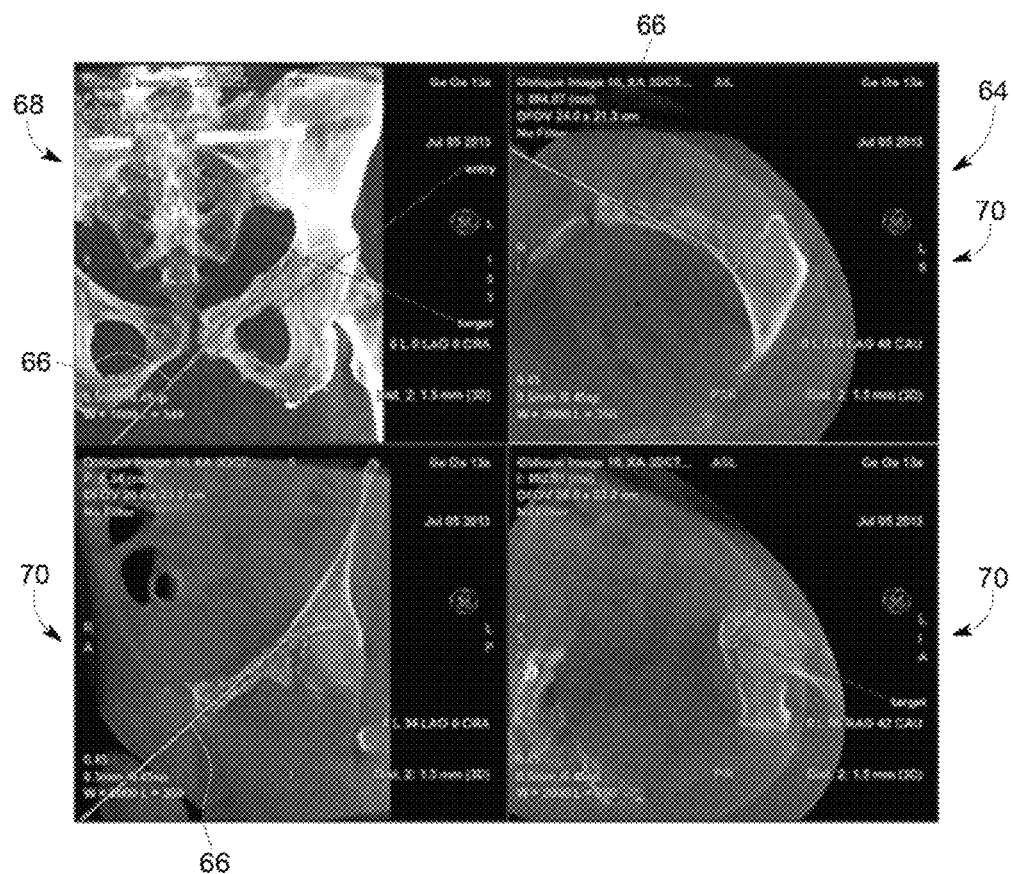
FIG. 6 depicts an exemplary embodiment of an instrument reconstruction.

At 110 the 3D reconstruction of an instrument is overlaid in the 3D reconstruction or cross sectional views, for example in an instrument reconstruction display 64 as depicted in FIG. 6. In the instrument reconstruction display 64, in FIG. 6, the reconstructed instrument 66 is presented in one or both of 3D reconstruction view 68 as well as 2D cross sectional views 70. While the reconstruction view 68 and the cross-sectional views 70 may be the same views as used during treatment planning, exemplarily depicted in FIG. 2, these views need not be the same.

Figure 8:
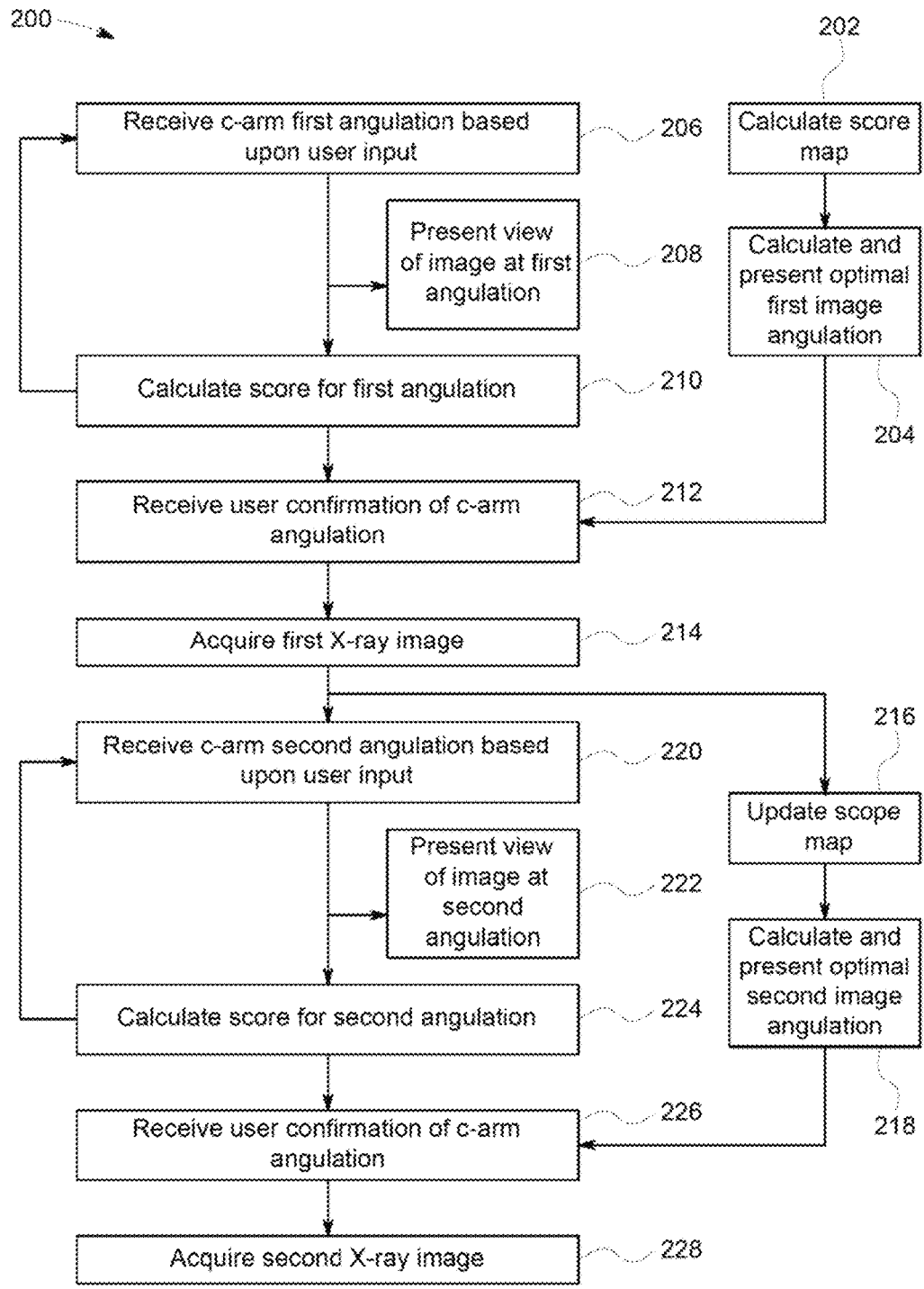
FIG. 8 is a flow chart that depicts an exemplary embodiment of a method of acquiring x-ray images for instrument reconstruction.

FIG. 8 depicts an exemplary embodiment of a method 200 of acquiring x-rays for instrument reconstruction. While techniques for the reconstruction of simple instruments from a limited number of x-ray views is known, the inventors have discovered that quality of the x-ray images used for such reconstruction is a significant contributor to the accuracy of the object reconstruction and positioning of that reconstructed object within a previously acquired 3D volume. Particularly, the geometry of the angulation of the acquired x-ray images with respect to the reconstructed object was found to be a significant factor in overall reconstruction quality.

Figure 9:
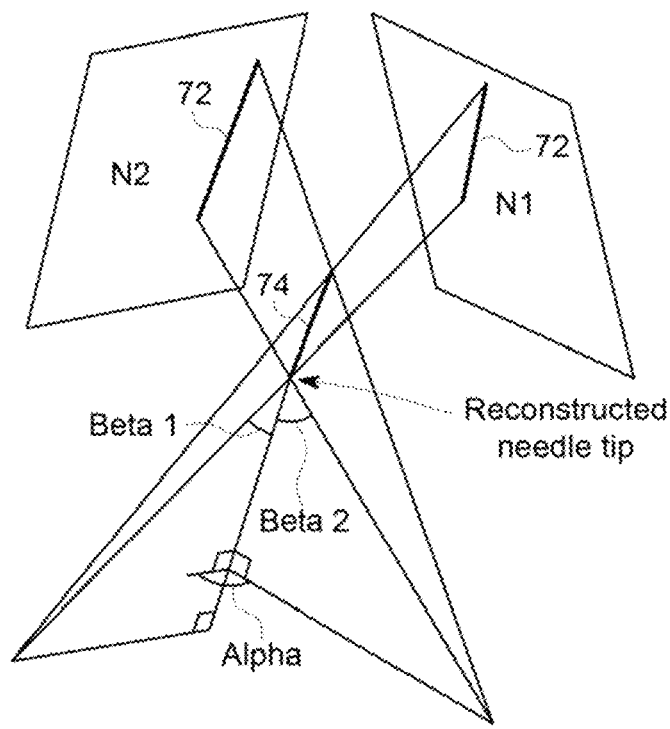
FIG. 9 diagrammatically depicts relevant geometry for the acquisition of x-ray images used for a 3D reconstruction of instruments.

FIG. 9 diagrammatically depicts relevant geometry between the first image N1 and second image N2. The instrument images 72 found in the first image N1 and second image N2 and the instrument reconstruction 74 created from those images.

The method 200 of acquiring X-rays for image reconstruction seeks to guide and inform the practitioner in obtaining x-ray images for improved instrument reconstruction and positioning within a 3D volume. In an embodiment, the method 200 can be a detailed embodiment of the steps carried out at 102 in the method 100. An exemplary embodiment of the method 200 begins at 202 with calculating a score map from the target trajectory and a predetermined simulation error for all possible combinations of first image angulation and second image angulation. In embodiments, a score map is pre-calculated. En embodiments, the score map is pre-calculated to improve real-time feed back of the score relative to an input or modified first image angulation as described in further detail herein. In some embodiments, the score map may be used to calculate the optimal angulations as described in further detail herein. Still further embodiments may operate without a score map. The target trajectory is previously calculated as described above during the trajectory planning prior to the surgical procedure.

Figure 10:
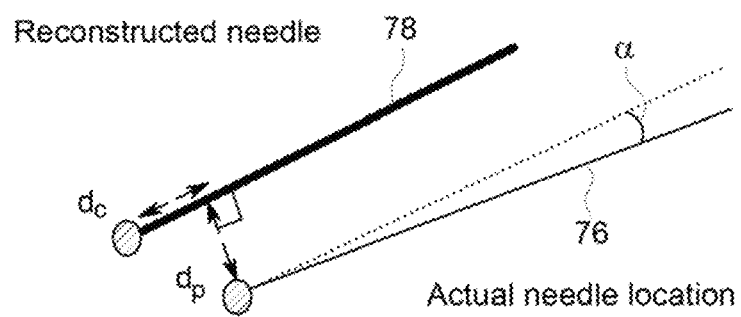
FIG. 10 diagrammatically decompose the three types of error in instrument reconstruction.

FIG. 10 diagrammatically depicts the three types of error in instrument reconstruction between an actual instrument 76 and the reconstructed instrument 78. These are represented as orthogonal distance ($d_p$), axial distance ($d_c$) and angle ($\alpha$). In embodiments, the inventors have found that of those three types of error, orthogonal distance ($d_p$) is the most clinically relevant in guided instrument procedures as error in that dimension is most likely to result in any chance to miss the intended anatomical target. Therefore, a predetermined simulation error (for example a distance or angle) is established for each of the error values ($d_p$, $d_c$, $\alpha$), with different values adjusted to match the clinical need. In exemplary embodiments, this predetermined simulation error may be 2.5 mm for dp and larger values for $d_c$ and $\alpha$. With these input values, a score map, which in an exemplary embodiment is a table of scores calculated based upon these values for any reachable pair of position of the acquisition system. As noted above, the C-arm position is exemplarily represented as a rotation about each axis (e.g. LAO/RAO, CRA/CAU, L).

In another embodiment, the score for each possible combination of first and second angulations is representative of an estimated simulation error calculated for a reconstruction along the target trajectory from first and second images having those angulations. In such an embodiment, a score representative of the reconstruction from each combination of available first and second images is calculated based upon the image set. In a further embodiment, the score in the score map is presented as a table of possible first image angulations. At each possible first image angulation, the score is based upon a selected best second image angulation. In embodiment, the score may be normalized to a scale of 1-100 or any other suitable scale. In other embodiments, the score is represented in bins defined by threshold values for the scores.

Figure 4B:
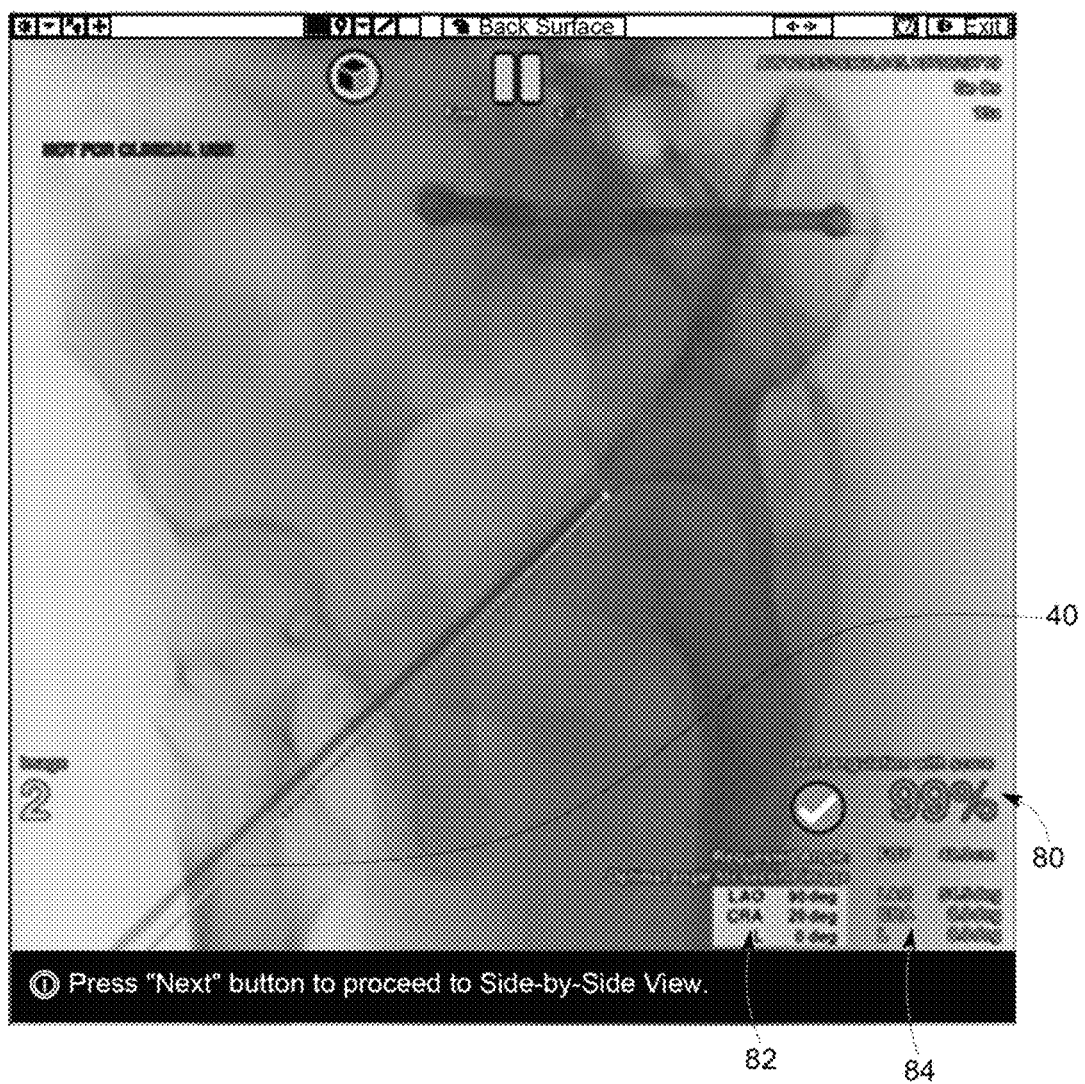
FIG. 4B depicts a display for acquisition of a second image.

FIGS. 4A and 4B exemplarily depict displays which may be presented on a graphical display device for acquisition of the first image (FIG. 4A) and the second image (FIG. 4B). In the images, the target trajectory 40 is depicted along with the score 80 calculated for an x-ray image taken of that view.

At 204, an optimal first image angulation is calculated and then may be presented. This is seen as the optimal angle indication 82 in FIGS. 4A and 4B. The calculation of the optimal angle may be a selection of the angulations associated with a highest score in the calculated score map, or may be further derived from the calculated score map to select an optimal angulation between all angulations having a maximum score based upon further considerations, including, but not limited to current C-arm position.

As mentioned above, in another embodiment the optimal first image angulation is calculated as an optimal image set, providing an optimal first image angulation and an optimal second image angulation. In an embodiment, the optimal image set may be selected from a combined score of the reconstruction from the first image angulation and second image angulation.

At 206 a user input of a C-arm first angulation is received, in one embodiment, the user enters one or more angulation settings for the C-arm. In a further exemplary embodiment, the user inputs the angulation of the C-arm which is represented in a movement of a presented 2D or 3D image. In exemplary embodiments, this may be a 3D volume registered to the 2D presentation of a fluoroscopic image or other x-ray. In another embodiment, the presented image is a volume or model representative of a portion of the patient's anatomy. The presented displays of FIGS. 4A and 4B can be manipulated by a user to rotate about the target trajectory. As these inputs are received, at 208 in some embodiments, the displays are modified to present the 3D image at the current C-arm angulation. The C-arm angulations associated to the user inputs and the currently presented image are presented at 84.

From the received user input of the C-arm angulation, a first score as described above is calculated for the current C-arm angulations at 210. In one embodiment, this may be calculated in real time as user inputs of the C-arm angulation are received. In another embodiment wherein a score map is calculated, the first score is calculated by identifying the score in the score map associated with the C-arm angulation. Thus, in embodiments, the practitioner is given real-time feedback regarding the potential accuracy of a reconstruction based upon an x-ray image acquired at the current C-arm angulations. Thus, the practitioner can continue to manipulate the view and C-arm angulations and the system receives further user inputs at 206 resulting in an updated score until the practitioner is satisfied with the applied C-arm angulation, score and display of 3D image. In an embodiment, the score may be presented as a percent on a normalized 0-100 scale. In one example of such an embodiment, a score of 90% or above may indicate an image angulation to achieve a desired quality (e.g. within 2.5 mm of reconstruction error), while 100% indicates the optimal potential angulations. Color coding of the score may also be used to provide a visual cue to the practitioner regarding the quality of the image for use in instrument reconstruction.

In embodiments, the practitioner may select the optimal angulation calculated at 204 and the system will navigate the C-arm to the calculated optimal C-arm angulation for the first image. However, as previously noted, a variety of angulations may be determined to have the potential result of the same or similar high score for potential reconstruction of the instrument. Additionally, the practitioner may have their own preferences regarding x-ray image angulations and desire to select their own image. However, with the real-time presentation of the calculated score, the practitioner is given the feedback to evaluate and select the angulation for acquisition of the x-ray images. As mentioned above, an optimal angulation for the first image may be calculated and determined as an optimal set of images, including at least a fast image. In such an embodiment, the user may be presented with the optimal angulation of a first image of the optimal image set.

At 212 a user confirmation of the first image C-arm angulation is received. While in an embodiment wherein a view of an image acquired at the first angulation is calculated and presented, the received user confirmation may confirm the current view and current angulation of the C-arm, in another embodiment as described, the system may receive a confirmation of a user selection of the presented optimal first image angulation. At 214 the C-arm control 30 of the system controller 14 operates the C-arm 12 (FIG. 1) to acquire the first x-ray image. In embodiments, the acquisition of the first x-ray image with the C-arm may require further practitioner inputs at control points and/or confirmation as would be recognized in the art.

At 216, in embodiments that employ a score map, the score map is updated with the information of the acquired first x-ray image. As noted above, the original calculation of the score map assumed all possible angulations for the other (second) image. Therefore, by updating the score map with the actual angulations of the first image, the score map is greatly refined relative to the angulation of the first x-ray image.

From the updated score map an optimal second image angulation can be calculated and presented at 218. As with the acquisition of the first image described above, the optimal angulation for the second image is presented to the practitioner and the practitioner may select that the second image be taken with these angulation coordinates. Alternatively, the practitioner can input a second C-arm angulation, which is received by the system at 220. As described above, the user input of the second C-arm angulation may be input as an entry of the C-arm angulation. In another embodiment, the user input of the second C-arm angulation may be a modification of an image presented on the display, entered by the user providing movement inputs that are received by the system at 220 to move the image presented on the display to the x-ray view that the practitioner desires to be acquired as the second x-ray image. Upon receipt of the C-arm second angulation, the system may present at 222 a view of an image at the second angulation. Received user inputs of the C-arm angulation may result in movement of the C-arm to the input angulation.

As with acquisition of the first image, the received second C-arm angulation coordinates may be presented back to the practitioner in the graphical display. The received C-arm second angulation coordinates are used to calculated a second score at 224 representative of the potential quality of a reconstruction of the instrument from a second x-ray image acquired at the second angulation of the C-arm. The score may be presented at 224 in a manner updated in real-time be reference to the score map with the current C-arm angulation coordinates. This gives the practitioner real-time feedback in selecting a view for the second x-ray image. As described above with respect to the first image, other embodiments may use the score map to referentially calculate the second score. In an embodiment with a pre-calculated score map updated for the second image, the received second angulation coordinates may be sought in the score map to identify the pre-calculated score associated with the received second angulation coordinates.

In embodiments, the received C-arm second angulation may be updated by the practitioner as the practitioner enters one or more possible C-arm angulations to evaluate for acquisition of the second image. As described above, in another embodiment the received input of the C-arm second angulation may be a practitioner selection of the calculated optimal second image angulation as presented at 218.

While embodiments have been described herein using a pre-calculated score map, in other embodiments, the score can be independently calculated each time new C-arm angulation coordinates are received from the practitioner. As that creates additional processing burdens, the inventors have found that pre-calculation of the score map and presentation of the score by way of reference to the score map improves user experience.

At 226 a user confirmation of the C-arm angulation for the second image is received. At 228, the C-arm control of the system controller and the C-arm are operated to acquire the second image at the second angulation. As with acquisition of the first image, operation of the C-arm to acquire the second image may require additional practitioner inputs and controls, including, but not limited to, confirmations of C-arm settings and actual image capture by the C-arm.

In exemplary embodiments in which more than two x-ray images are acquired, the method may proceed in a similar manner wherein the scores for the plurality of angulations for the subsequent (e.g. third) image are calculated based upon the previously acquired images. For example, an image that duplicates the view provided by the first image or the second image would be undesirable as a third image as it does not provide additional information to improve instruments reconstruction. Such embodiments may be useful in performing reconstructions of complex structures such as but not limited to multiple needles, curved guide wires, and guide wires or other instruments navigated through tortuous vessels.

Exemplary embodiments as disclosed herein, calculate the score based upon image angulation and the target trajectory. Still further embodiments may incorporate additional considerations in determining the score. The addition of further considerations may further help to differentiate between similarly scored image angulations for selection of suggested optimal image. Refined score may also further differentiate between possible image views. Examples of additional considerations may include detection of further objects of interest in the image. Other objects such as, but not limited to, patient anatomy and/or the actual instrument may be detected and used to refine the score. Also a projection matrix in the Interventional System Reference Frame (ISRF) can be estimated for views and incorporated into the score. In additional embodiments, the potential accuracy of 3D registration between the ISRF and the patient volume can be considered, including, but not limited to initial placement of the patient volume in the ISRF and an assessment of an ability to manually or automatically compensate for mis-registration after reconstruction.

In still further exemplary embodiments, the images for instrument reconstruction may be acquired without reference to a target trajectory. Rather, the images for instrument reconstruction may be acquired with reference to an initial reconstruction. An initial instrument reconstruction may be performed with the acquisition of at least one additional x-ray image. As noted above, without angulation optimization, instrument reconstructions may suffer from error. However, such reconstruction may, in embodiments, may provide a suitable representation of instrument location from which to calculate image scores and/or optimal image angulations for a subsequent refined reconstruction of the instrument.

In one exemplary embodiment, two initial x-ray images are acquired and an initial instrument reconstruction is calculated from the initial images. This initial reconstruction is then used as an input in calculating the scores for the first and second images used in the subsequent final reconstruction of the instrument in the manner as described above.

In another embodiment, an initial x-ray image is acquired. From the initial x-ray image, at least one of two scores may be calculated to assist in selection of at leas tone or more subsequent x-rays. The first scores based upon the initial image and the achievable final accuracy of a reconstruction considering all possible angulations for a subsequently acquired image. This is similar to the score as calculated as described above with respect to the first image. Additionally, a score that describes a current reconstruction accuracy may be calculated. This score is calculated assuming that no subsequent images will be acquired after the images acquired at the current angulation. This score is similar to that as calculated above with respect to the second view. The method may progress to capture additional x-ray images in a manner to maximize both of the scores. Additionally, once the initial x-ray image and the first x-ray image are acquired, an initial reconstruction of the instrument is feasible. This initial reconstruction, as described above, may be used in calculating a score for an optimized angulation for a second or subsequent x-ray image or may be evaluated on its own for accuracy for a reconstruction. In an embodiment wherein the initial reconstruction is evaluated as accurate, such initial reconstruction may be used.

An extension of the embodiments described above may be implemented to result in an automated instrument reconstruction work flow. Starting from an initial x-ray image, by implementing the methods as described above in an automated sequence, an optimal angulation for a first image may be calculated and the C-arm automatedly operated to acquire a first image at the calculated optimal angulation. Using one or more of the initial image, the acquire first image, and an initial reconstruction between the first image and the initial image, an optimal angulation for a second or subsequent image may be calculated and the C-arm operated to acquire the second or subsequent image at the calculated optimal angulation. Such an automated workflow may continue until an instrument reconstruction of a sufficient evaluated quality is achieved.

In an additional embodiment, such reconstruction accuracy score may be presented to a user for final confirmation of a sufficient accuracy score and acceptance of the reconstruction.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of object reconstruction from x-ray imaging, the method comprising:
receiving an input of a first angulation for a first x-ray;
calculating a first score representative of a quality of a reconstruction of an object from an x-ray image acquired at the first angulation;
acquiring a first x-ray image at the first angulation;
receiving an input of a second angulation for a second x-ray;
calculating a second score representative of the quality of the reconstruction of the object from the first x-ray image and an x-ray image acquired at the second angulation;
acquiring a second x-ray image at the second angulation; and
reconstructing the object from the first x-ray image and the second x-ray image.

2. The method of claim 1 further comprising:
presenting the first score on a graphical display;
receiving a user input confirming the first angulation;
presenting the second score on the graphical display; and
receiving a user input confirming the second angulation.

3. The method of claim 1 further comprising:
pre-calculating scores representative of a quality of reconstruction of an object for a plurality of combinations of the first angulation and the second angulation;
selecting an optimal combination of the first angulation and the second angulation based upon the pre-calculated scores; and
presenting the selected optimal combination of the first angulation and the second angulation.

4. The method of claim 1, further comprising:
receiving an updated input of the first angulation for the first x-ray;
calculating an updated first score; and
presenting in real-time on the graphical display, an updated first score for the first x-ray.

5. The method of claim 1 further comprising:
presenting an initial view of a volume representing patient anatomy on a graphical display;
receiving a first user movement of the volume representing patient anatomy as the input of the first angulation for the first x-ray; and
receiving a second user movement of the volume representing patient anatomy as the input of the second angulation for the second x-ray.

6. The method of claim 5, further comprising:
presenting the first score on the graphical display; and
presenting the second score on the graphical display;
wherein calculating the first score is performed in real-time with receipt of the first user movement and calculating the second score is performed in real-time with receipt of the second user movement.

7. The method of claim 1 wherein calculating the first score comprises pre-calculating scores for a plurality of possible angulations for the first angulation based upon a plurality of possible angulations for the second angulation and calculating the second score comprises pre-calculating scores for a plurality of possible angulation for the second angulation.

8. The method of claim 1, wherein the object is a surgical instrument.

9. The method of claim 8, wherein the first score is calculated further based upon a calculated target trajectory of the surgical instrument.

10. The method of claim 1, further comprising:
calculating an optimal angulation for the first x-ray image;
presenting the optimal angulation on a graphical display;
calculating an optimal angulation for the second x-ray image;
presenting the optimal angulation of the graphical display.

11. The method of claim 10, wherein the optimal angulation for the first x-ray image and the optimal angulation for the second x-ray image are an optimal pair of angulations from a plurality of calculated pairs of angulations for the first x-ray image and the second x-ray image.

12. A method of reconstruction of a surgical instrument, the method comprising:
calculating a first plurality of scores for each of a plurality of possible angulations of a first x-ray from a surgical instrument target trajectory;
receiving an input of a first angulation for the first x-ray;
acquiring a first x-ray image at the first angulation with an x-ray c-arm;
calculating a second plurality of scores for each of a plurality of possible angulations of a second x-ray from the surgical instrument target trajectory and the first x-ray image;
receiving an input of a second angulation for the second x-ray;
acquiring a second x-ray image at the second angulation with the x-ray c-arm; and
reconstructing the surgical instrument from the first x-ray image and the second x-ray image.

13. The method of claim 12 further comprising:
presenting a first score from the plurality of scores, updated in real-time according to the input of the first angulation; and
presenting a second score from the second plurality of scores, updated in real-time according to the input of the second angulation.

14. The method of claim 12, further comprising:
determining a first optimal angulation for the first x-ray image from the first plurality of scores;
upon receiving a user input, operating the x-ray c-arm to the first optimal angulation;
determining a second optimal angulation for the second x-ray image from the second plurality of scores; and
upon receiving a user input, operating the x-ray c-arm to the second optimal angulation.

15. The method of claim 14, further comprising:
presenting the first optimal angulation for the first x-ray image; and
presenting the second optimal angulation for the second x-ray image.

16. The method of claim 12 wherein the first plurality of scores and the second plurality of scores are calculated for a plurality of image sets comprising a first image of the first angulation and a second image of the second angulation prior to acquiring the first image and the second image.

17. The method of claim 16 further comprising calculating a score representative of a quality of a reconstruction from each image set of the plurality of image sets.

18. A system for surgical instrument reconstruction, the system comprising:
an x-ray C-arm comprising an emitter and a detector, the x-ray C-arm movable about a plurality of axes and operable to acquire x-ray images of a patient at a plurality of angulations about the plurality of axes;
a graphical display configured to present a volume representing patient anatomy; and a controller communicatively connected to the x-ray C-arm and the graphical display, the controller receives an input of a first angulation for a first x-ray, calculates a first score representative of a quality of a reconstruction of the surgical instrument from an x-ray image acquired at the first angulation, and operates the graphical display to present the first score, the controller operates the x-ray C-arm to acquire a first x-ray image, the controller receives an input of a second angulation for a second x-ray, calculates a second score representative of a quality of a reconstruction of the surgical instrument from an x-ray image acquired at the second angulation and the first x-ray image, and operates the graphical display to present the second score, the controller operates the x-ray C-arm to acquire a second x-ray image, and the controller reconstructs a surgical instrument from the first x-ray image and the second x-ray image and presents the reconstructed surgical instrument in at least one of a 2D image and a 3D image on the graphical display.

19. The system of claim 18 wherein the x-ray C-arm is a biplane C-arm comprising a first x-ray C-arm and a second x-ray C-arm, wherein the first x-ray image is acquired by the first x-ray C-arm and the second x-ray image is acquired by the second x-ray C-arm.

20. The system of claim 18 wherein the controller operates the C-arm to acquire an initial x-ray image, the controller calculates the first score based in part upon the initial x-ray image, the controller calculates an initial reconstruction from the initial x-ray image and the first x-ray image, and the controller calculates the second score based in part upon the initial reconstruction.

* * * * *